United States Patent [19]

Chanoch

[11] Patent Number: 5,674,204
[45] Date of Patent: Oct. 7, 1997

[54] MEDICATION DELIVERY PEN CAP ACTUATED DOSE DELIVERY CLUTCH

[75] Inventor: Lawrence H. Chanoch, Mahwah, N.J.

[73] Assignee: Becton Dickinson and Company, Franklin Lakes, N.J.

[21] Appl. No.: 530,556

[22] Filed: Sep. 19, 1995

[51] Int. Cl.⁶ .................................................. A61M 5/00
[52] U.S. Cl. ............................ 604/211; 604/207; 604/232
[58] Field of Search ..................... 604/110, 187, 604/186, 188, 192, 195, 196, 221, 207–211, 232, 218

[56] References Cited

U.S. PATENT DOCUMENTS

| | | | |
|---|---|---|---|
| 4,973,318 | 11/1990 | Holm et al. | 604/208 |
| 5,112,317 | 5/1992 | Michel | 604/208 |
| 5,273,544 | 12/1993 | Van Der Wal | 604/134 |
| 5,279,586 | 1/1994 | Balkwill | 604/207 |
| 5,370,629 | 12/1994 | Michel et al. | 604/207 |
| 5,383,865 | 1/1995 | Michel | 604/232 |
| 5,582,598 | 12/1996 | Chanoch | 604/208 |

FOREIGN PATENT DOCUMENTS

| | | | |
|---|---|---|---|
| 0409365 | 1/1991 | European Pat. Off. | 604/187 |
| 3010838 | 6/1993 | WIPO | 604/187 |

*Primary Examiner*—Corrine M. McDermott
*Assistant Examiner*—Cris L. Rodriguez
*Attorney, Agent, or Firm*—Alan W. Fiedler

[57] ABSTRACT

A medication delivery pen is provided having a medication cartridge assembly, a pen body assembly and a cap. The pen body assembly includes a dose setting mechanism and a dose delivery mechanism that are selectively disconnected and connected by attaching and removing, respectively, the cap of the medication delivery pen. When the cap is attached to the medication delivery pen the user can easily dial in and correct the dialed in dosage and when the cap is removed the medication delivery pen is ready to dispense the dialed in dosage.

9 Claims, 5 Drawing Sheets

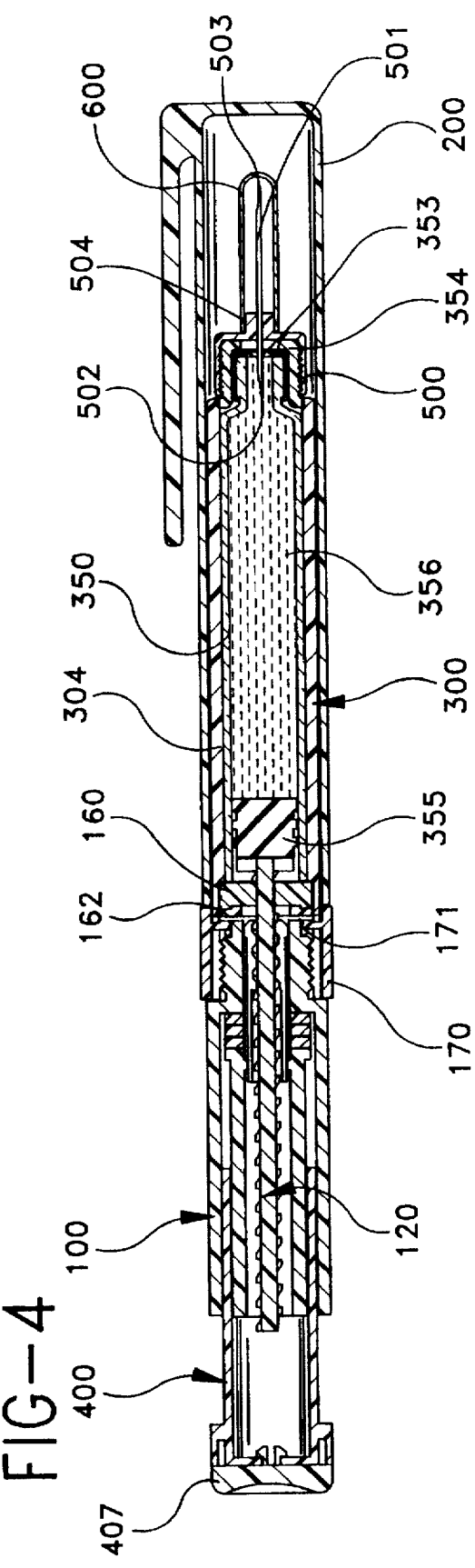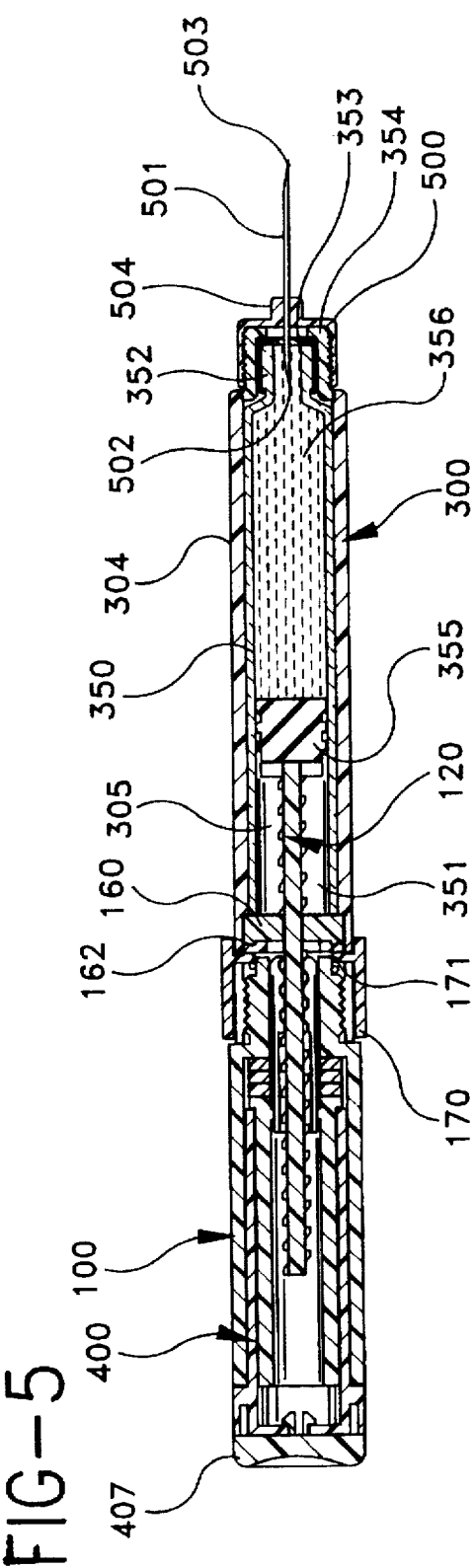

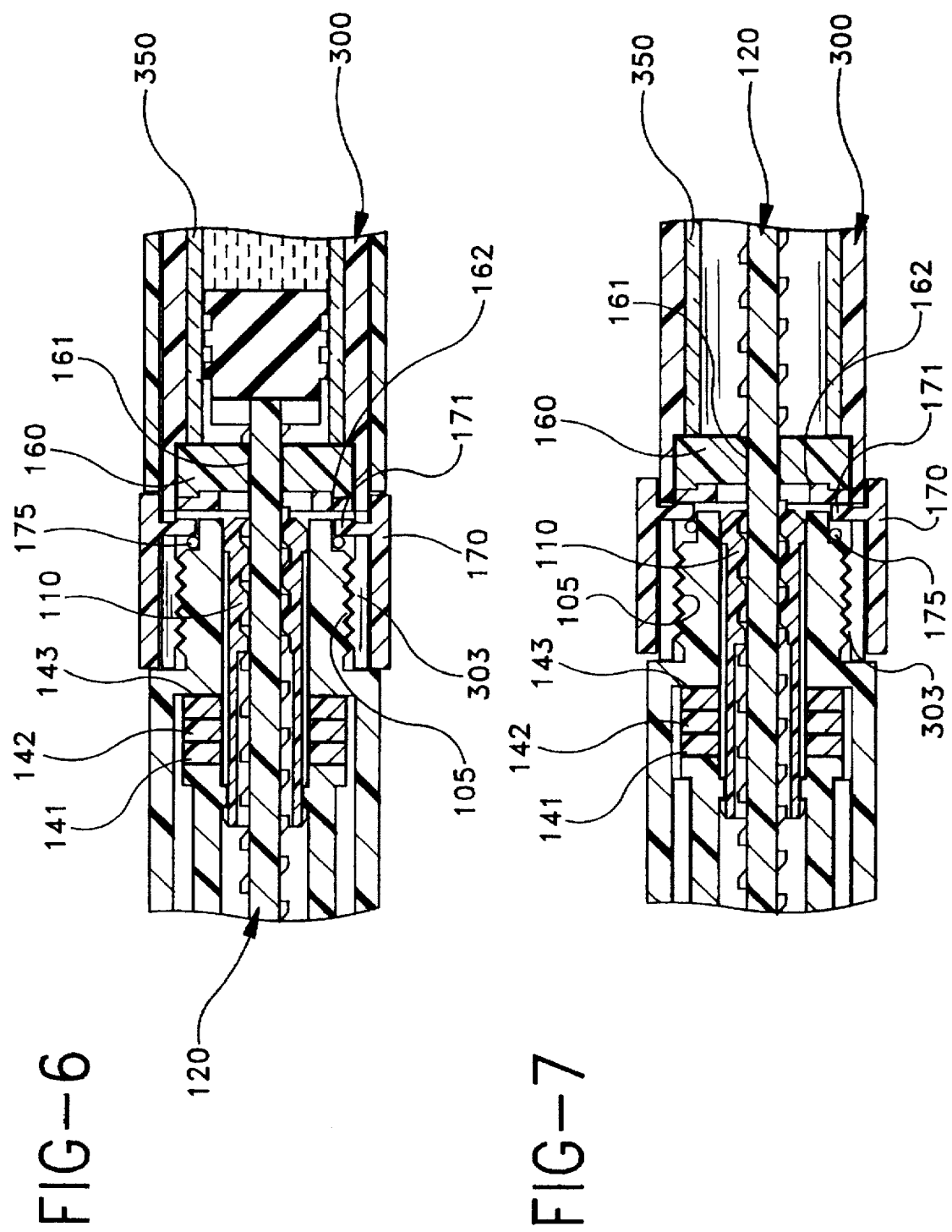

MEDICATION DELIVERY PEN CAP ACTUATED DOSE DELIVERY CLUTCH

BACKGROUND OF THE INVENTION

1. Field of the Invention

The subject invention relates to a medication delivery pen having a cap actuated clutch that disconnects a dose setting mechanism from a dose delivery mechanism when the pen is capped and connects the dose setting mechanism to the dose delivery mechanism when the pen is uncapped.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula is mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal and accessed by piercing the elastomeric seal with the needle cannula. A selected dose of the medication may be drawn into the chamber of the syringe barrel by moving the plunger a selected distance in a proximal direction. The needle cannula is then withdrawn from the vial, and the medication is injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-adminstration of medication. One prior art medication delivery pen includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point of the needle cannula pierces the elastomeric seal on the vial. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above.

The above described reusable medication delivery pen is effective and much more convenient for self-administration of medication than the typical hypodermic syringe and separate medication vial. However, the disassembly of the pen to remove empty medication vials and to insert new ones is an inconvenience. As a result, disposable pens have been developed. The prior art disposable medication delivery pen includes a vial of insulin or other such medication permanently encapsulated therein.

The patient need merely connect a double-ended needle cannula to the disposable pen for each administration of medication. The prior art disposable pen can be discarded when the supply of medication permanently encapsulated therein has been exhausted.

Disposable medication delivery pens offer certain conveniences to the patient who is required to self-administer medication. However, the dose selecting and driving mechanisms of prior art medication delivery pens are fairly complex devices and costly to manufacture. Hence, a substantial cost penalty is associated with the convenience of using a disposable medication delivery pen.

Another problem with the above-described medication delivery pens is with the difficulty in setting the desired dose caused by space limitations on the dose setting mechanism for dose indicating numbers. For example, the dose setting mechanism may not be able to make more than one full rotation and will therefore require space for a return track to correct for dose settings higher than desired.

SUMMARY OF THE INVENTION

It is an objective of the present invention to overcome the above problems of the prior art by providing a medication delivery pen having a cap actuated clutch that automatically disconnects a dose setting mechanism from a dose delivery mechanism when the pen is capped and automatically connects the dose setting mechanism to the dose delivery mechanism when the pen is uncapped. Such an arrangement provides for a multi-turn dose setting knob to be used in the medication delivery pen, since the connect/disconnect clutch between the dose setting mechanism and the dose delivery mechanism permits the dose setting knob to be turned in both an up direction and a down direction when the cap is attached and eliminates the need for a return track.

In particular, the medication delivery pen of the present invention includes a medication cartridge assembly that is selectively engageable with and disengageable from a pen body assembly containing the cap actuated connect/ disconnect clutch. The medication cartridge assembly is an elongate generally cylindrical structure having opposed proximal and distal ends. The distal end of the medication cartridge assembly includes needle mounting means for securely but releasably receiving a needle cannula assembly and a pierceable elastomeric seal that may be repeatedly and resealable pierced by the proximal end of a double-ended needle cannula. The proximal end of the medication cartridge assembly includes body mounting means for securely but releasably mounting the medication cartridge assembly to the pen body assembly. The medication cartridge assembly further includes plunger means slidably disposed in fluid tight engagement therein that is initially disposed in a proximal position within the medication cartridge assembly and can be moved in a distal direction by a lead screw projecting from the pen body assembly.

The pen body assembly comprises an array of mounting threads to enable threaded engagement of the pen body assembly and the medication cartridge assembly. The pen body assembly further includes the lead screw for selectively engaging the plunger of the disposable cartridge assembly and for urging the plunger of the disposable cartridge assembly in a distal direction. At least a portion of the lead screw has driving threads engaged with other portions of the pen body assembly that are operative to achieve axial movement of the lead screw in response to axial forces exerted on a rotatable actuator button mounted on the proximal end of the pen body assembly. The driving threads define the same pitch and direction as the mounting threads of the pen body assembly. As will be explained in greater detail below, this design facilitates quick connection of the pen body assembly to the medication cartridge assembly, and further assures a virtually automatic return of the lead screw to a start position each time a new medication cartridge assembly is mounted to the pen body assembly.

The pen body assembly also includes a connect/ disconnect clutch that causes the lead screw to engage with tabs on an anti-rotation ring to prevent relative rotation between the lead screw and the disposable cartridge assembly when the pen is not capped. When the pen is capped, the connect/disconnect clutch causes the anti-rotation ring to disengage from the lead screw and permits the lead screw to be free to rotate relative to the disposable cartridge assembly.

The pen body assembly further comprises a dose setting means for establishing and precisely controlling the amount of medication to be delivered in response to each actuation of the actuator button. The dose setting means may be any of several structures one of which is described in greater detail below.

These and other aspects, features and advantages of the present invention will become apparent from the following detailed description taken in conjunction with the accompanying drawings.

DESCRIPTION OF THE DRAWINGS

FIG. 4 is a longitudinal cross-sectional view of the medication delivery pen shown in FIG. 1 with the cap thereon;

FIG. 5 is a longitudinal cross-sectional view of the medication delivery pen shown in FIG. 1 without the cap;

FIG. 6 is an enlarged cross-sectional view of the connect/ disconnect clutch section of the medication delivery pen shown in FIG. 4 with the clutch disengaged; and FIG. 7 is an enlarged cross-sectional view of tile connect/ disconnect clutch section of the medication delivery pen shown in FIG. 5 with the clutch engaged.

DETAILED DESCRIPTION

Figure 1:
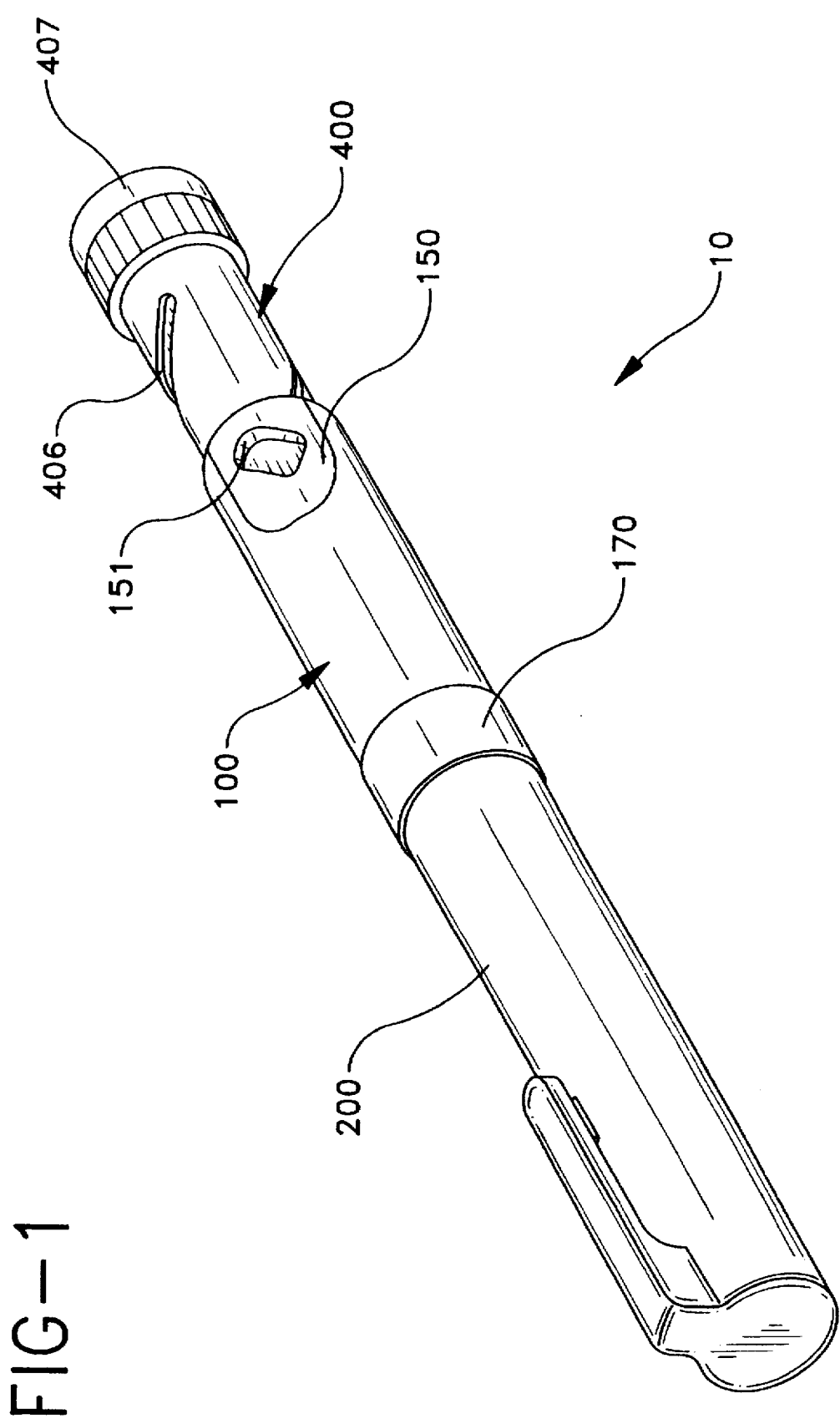
FIG. 1 is a perspective view of the medication delivery pen of the subject invention.
Figure 2:
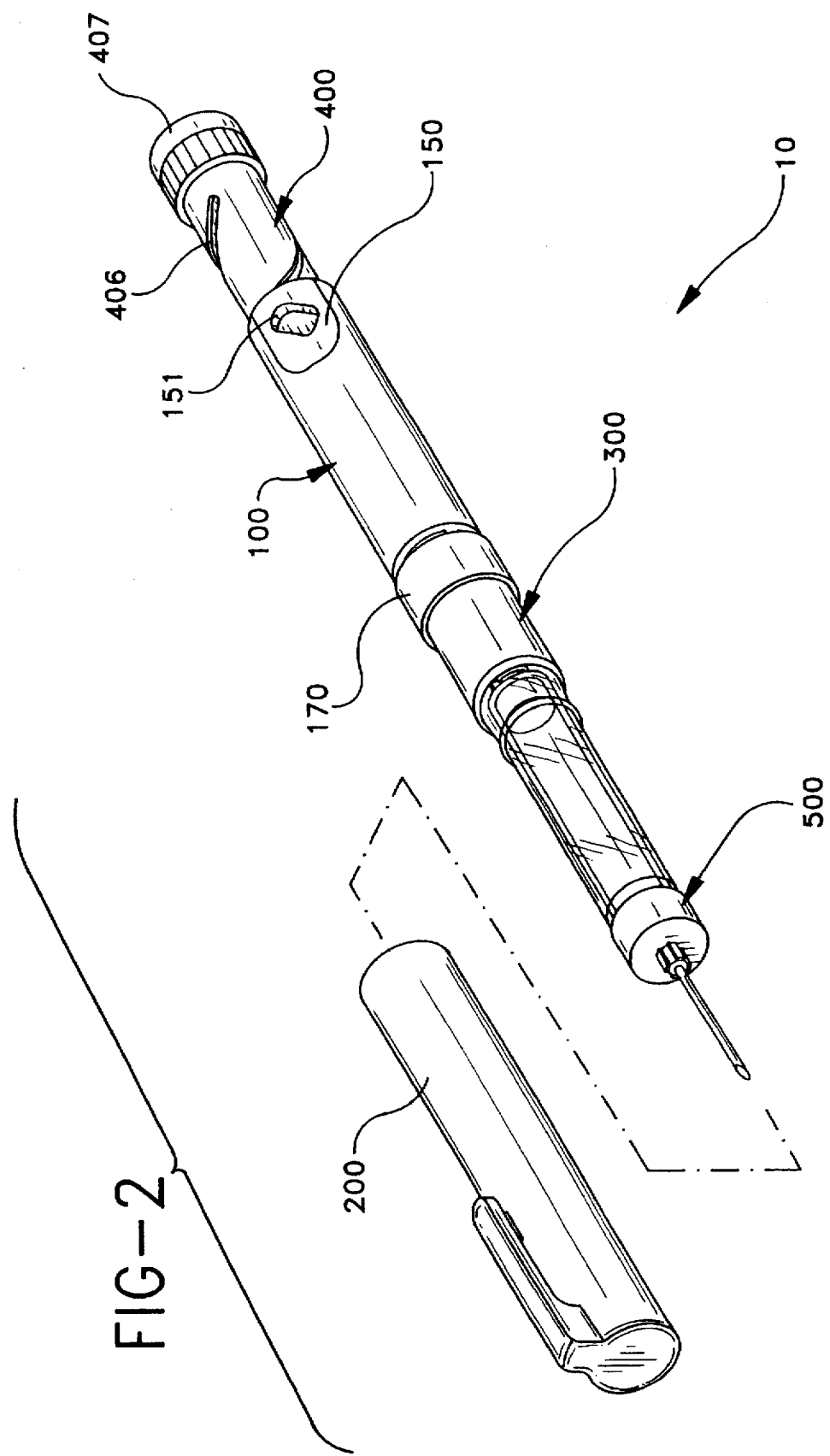
FIG. 2 is a perspective view of the pen body assembly of the medication delivery pen shown in FIG. 1 with the cap removed.
Figure 3:
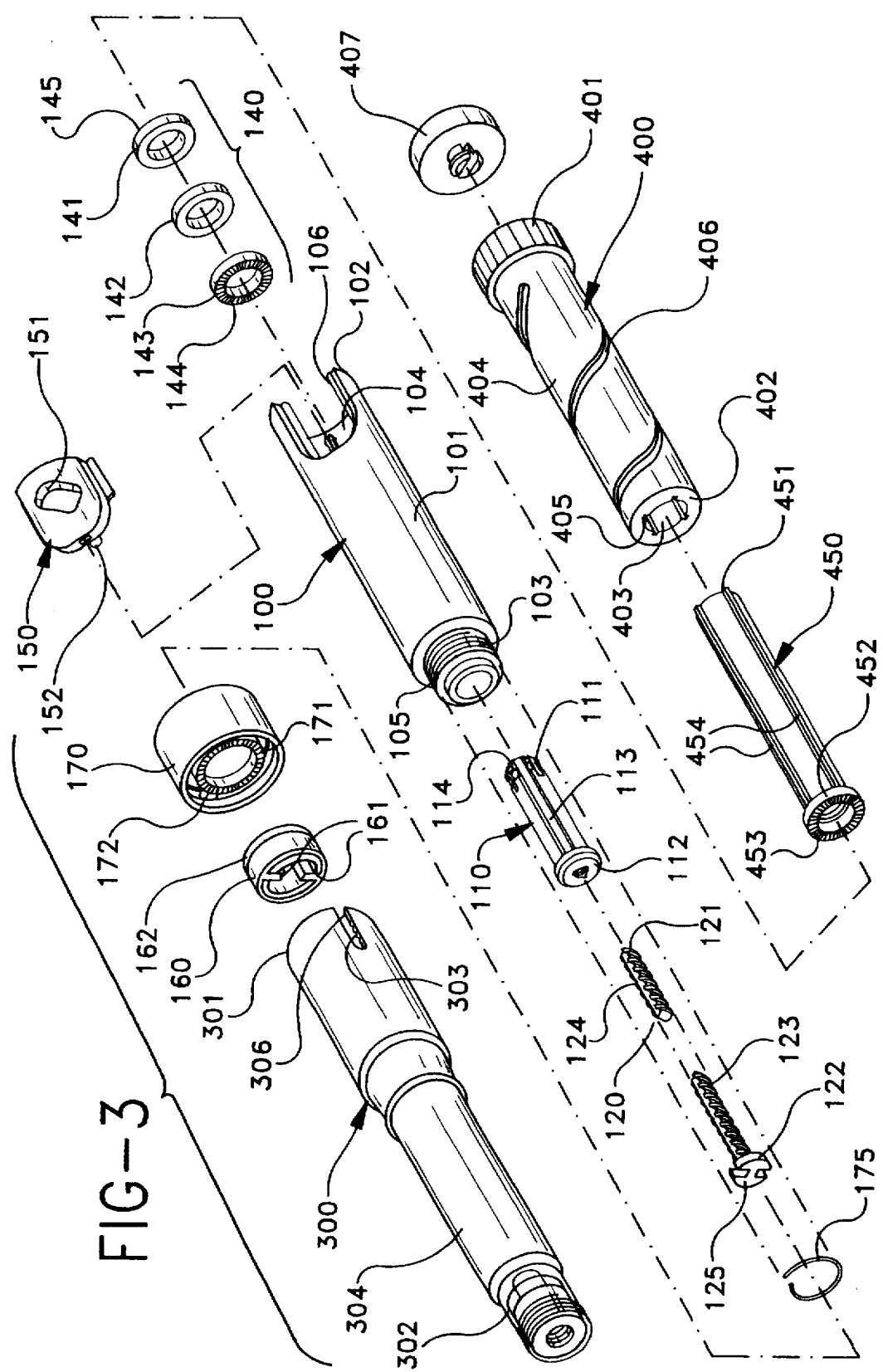
FIG. 3 is a exploded perspective view of tile pen body assembly of the medication delivery pen shown in FIG. 1.

A medication delivery pen in accordance with tile subject invention is identified generally by the numeral 10 in FIGS. 1-7. Medication delivery pen 10, as shown in FIGS. 1, 2 and 3, includes a pen body assembly 100, a cap 200, a cartridge assembly 300, and a needle cannula assembly 500. Cartridge assembly 300 includes opposed proximal and distal ends 301 and 302, respectively. Proximal end 301 of cartridge assembly 300 is dimensioned and configured to threadedly engage pen body assembly 100 and includes a pair of slots 306, as explained further herein. Distal end 302 of cartridge assembly 300 is configured to securely but releasably engage needle cannula assembly 500.

The preferred embodiment of pen body assembly 100 is illustrated in detail in FIGS. 1-7. It is understood, however, that variations from this preferred embodiment may be provided, and are considered to be within the scope of the subject invention. Pen body assembly 100 includes a generally cylindrical housing 101 having opposed proximal and distal ends 102 and 103, and a substantially hollow throughbore 104 extending axially therethrough. An army of external threads 105 extends proximally from distal end 103 for threaded engagement with threads 303 in proximal end 301 of cartridge assembly 300. Portions of hollow throughbore 104 of housing 101 adjacent distal end 103 are characterized by an array of clutch teeth (not shown) molded therein. Proximal end 102 of housing 101 is characterized by a cut-out 106 formed therein for receiving a window insert 150 having a window 151 and a button 152.

Pen body assembly 100 further includes a nut 110 having opposed proximal and distal ends 111 and 112, respectively. Exterior surface regions of nut 110 between proximal and distal ends 111 and 112 define a plurality of longitudinally extending splines 113. Proximal end 111 of nut 110 is characterized by a plurality of longitudinally extending resilient fingers 114 with enlarged ends that enable snap engagement of nut 110 into other portions of pen body assembly 100 as explained further herein. Distal end 112 of nut 110 is radially enlarged to limit axial movement of nut 110 into distal end 103 of housing 101. Thus, nut 110 is axially constrained within housing 101. However, the dimensions and configurations of nut 110 and housing 101 permit free relative rotation therebetween.

Pen body assembly 100 further includes a clutch assembly 140 having a proximal clutch 141, a distal clutch 143 and an annular spring 142 biasingly engaged therebetween. Proximal and distal clutches 141 and 143 are both configured for nonrotatable engagement over splines 113 of nut 110. Distal clutch 143 includes an array of distally facing saw teeth 144 dimensioned, disposed and configured for engagement with the teeth (not shown) on the interior of housing 101, such that distal clutch 143 can rotate only in one direction relative to housing 101. Proximal clutch 141 includes an array of proximally facing teeth 145 which are also configured for unidirectional rotation as explained further herein.

Pen body assembly 100 further includes a generally cylindrical driver 450 having opposed proximal and distal ends 451 and 452. Driver 450 is slidably inserted into housing 101 of pen body assembly 100 such that distal end 452 of driver 450 is snap fit over the enlarged ends of resilient fingers 114 at proximal end 111 of nut 110. This snap fit engagement prevents axial movement between nut 110 and driver 450, but permits free relative rotational movement within housing 101. Distal end 452 of driver 450 is also characterized by an array of saw teeth 453 that engage with the saw teeth 145 on proximal clutch 141. Outer surface regions of driver 450 are characterized by splines 454 extending radially outwardly thereon and along a substantial portion of the length of driver 450.

Pen body assembly 100 further includes a dose knob 400 which is a hollow generally cylindrical structure having opposed proximal and distal ends 401 and 402 and opposed inner and outer surfaces 403 and 404. Inner surface 403 is characterized by longitudinally extending grooves 405 which are disposed and dimensioned for engagement with splines 454 on driver 450. More particularly, dose knob 400 is spline mounted over driver 450 within housing 101 of pen body assembly 100. Thus, axially extending grooves 405 in dose knob 400 engage splines 454 of driver 450 to prevent relative rotation therebetween, but permitting relative axial movement. Outer surface 404 of dose knob 400 is characterized by a helical groove 406 with dosage indicia to define dose amounts corresponding to different positions along helical groove 406, as explained further herein. Helical groove 406 wraps around dose knob 400 a number of times to permit numerous rotations of dose knob 400. Proximal end 401 of dose knob 400 is characterized by a gnarled exterior surface to facilitate manipulation for setting a selected dose having an actuator button 407 snapped therein to permit relative rotation therebetween.

Insert 150 is snapped into engagement with cut-out 106 in the proximal end 102 of housing 101. Insert 150 includes a window 151 therethrough and a button 152 on an interior face that is dimensioned and disposed to engage with helical groove 406 on dose setting knob 400. Button 152 and window 151 are disposed to also enable the dosage indicia on dose setting knob 400 to be visible through window 151 as dose knob 400 is rotated.

Pen body assembly 100 includes a lead screw 120 with opposed proximal and distal ends 121 and 122 and an array of external threads 123. External threads 123 are characterized, however, by a pair of opposed axially extending grooves 124 which extend from an enlarged head 125 at distal end 122 substantially to the proximal end 121. Threads 123 are threadably engaged in nut 110, such that proximal end 121 of lead screw 120 is within housing 101 and distal end 122 projects distally beyond housing 101. Threads 123 on lead screw 120 have exactly the same pitch and the same hand as threads 105 on distal end 103 of housing 101.

Pen body assembly 100 further includes an anti-rotation ring 160 having a pair of tabs 161 extending therein and clutch teeth 162 on its proximal surface. Each tab 161 slidable engages groove 124 on lead screw 120 to allow anti-rotation ring 160 to travel on and rotate with lead screw 120. Thus, lead screw 120 can slidably move relative to anti-rotation tabs 161, but is prevented from rotating relative to tabs 161. Pen body assembly 100 also includes a connect/disconnect clutch 170 a pair of projections 172 that are received by slots 306 on cartridge assembly 300. Connect/disconnect clutch 170 also includes Clutch teeth 171 that engage with or disengage from clutch teeth 162 on anti-rotation ring 160, when cap 200 is on or off pen body assembly 100, respectively. For example, when cap 200 is not attached to pen body assembly 100 as shown in FIGS. 2, 5 and 7, clutch teeth 171 on clutch 170 are urged in a proximal direction by a spring 175 to engage with clutch teeth 162 on anti-rotation ring 160 and thereby prevent rotation of lead screw 120. However, when cap 200 is mounted on pen body assembly 100, clutch 170 is disengaged from antirotation ring 160 so that lead screw 120 is free to rotate in both directions to permit a user to easily set and modify the desired dosage by rotating the dose setting knob 400.

Pen body assembly 100 is assembled by placing nut 110 into housing 101 from distal end 103. Clutch assembly 140 then is mounted over splines 113 on nut 110. Driver 450 is then inserted into proximal end 102 of housing 101, and is urged sufficiently in a distal direction for snap fit engagement with nut 110. In this snapped engagement, saw teeth 144 of distal clutch 143 will be secured in engagement with the teeth in housing 101, and the saw teeth 145 of proximal clutch 141 will be engaged with saw teeth 453 at distal end 452 of driver 450. Spring 142 will maintain constant selected pressure between these interengaged saw teeth. Insert 150 then is positioned over dose knob 400 such that button 152 of insert 150 is engaged in the helical groove 406 in dose knob 400. The temporarily assembled insert 150 and dose knob 400 then are urged into housing 101. Lead screw 120 then is threaded into nut 110, and actuator button 407 is snapped into engagement with proximal end 401 of dose knob 400.

Cartridge assembly 300, shown in detail in FIGS. 2, 4 and 5, includes a molded housing 304 which extends from proximal end 301 to distal end 302 of cartridge assembly 300. Housing 304 includes a mounting cavity 305 extending inwardly from proximal end 301. Mounting cavity 305 is characterized by an array of internal threads 303 for threaded engagement with external threads 105 on distal end 103 of housing 101. Slots 306 located on proximal end 301 of cartridge holder assembly 300 receive projections 172 on clutch 170 when cartridge holder assembly 300 is threaded onto housing 101 to prevent clutch 170 from rotating with respect to lead screw 120.

Cartridge assembly 300, further includes a medication cartridge 350 securely retained in housing 304 between proximal end 301 and distal end 302 of cartridge assembly 300. Medication cartridge 350 includes an open proximal end 351 and a distal end 352 having a pierceable elastomeric seal 353 securely mounted thereto. A cap 354 extends between housing 304 and cartridge 350 for securely and permanently holding medication cartridge 350 in housing 304. A plunger 355 is disposed in sliding fluid tight engagement in cartridge 350. As shown in FIG. 4, plunger 355 initially is disposed substantially adjacent proximal end 351 of medication cartridge 350. Portions of cartridge 350 between plunger 355 and seal 353 are filled with a medication 356, such as insulin.

Needle cannula assembly 500 includes a double ended needle cannula 501 having opposed proximal and distal points 502 and 503, respectively, and a lumen extending axially therebetween. A mounting hub 504 is engaged on needle cannula 501 and is removably engageable with cap 354 of cartridge holder assembly 300. The relative location of mounting hub 504 ensures that proximal point 502 of needle cannula 501 will pierce seal 353 when mounting hub 504 is engaged with cap 354. Needle cannula assembly 500 further includes a shield 600 removably mounted thereon for protecting against accidental needle sticks until immediately prior to use of pen 10.

As noted above, pen body assembly 10 is reusable and cartridge holder assembly 300 is disposable. More particularly, cartridge 350 in cartridge holder assembly 300 will contain a volume of medication 356 sufficient for administration of several doses. After exhaustion of the medication 356, cartridge holder assembly 300 will be threadedly disengaged from pen body assembly 100 and discarded. A new cartridge holder assembly 300 may then be mounted to the pen body assembly 100. To effect the mounting of a new cartridge holder assembly 300 to the pen body assembly 100, the patient need merely advance distal end 122 of lead screw 120 into cartridge holder assembly 300 until distal end 122 of lead screw 120 engages plunger 355. Assembly continues by merely exerting axial forces on actuator button 407 and on cartridge holder assembly 300 Additionally, friction between plunger 355 and cartridge 350 and fluid forces exerted by medication 356 and seal 353 will prevent axial advancement of lead screw 120 beyond the position depicted in FIG. 4 during assembly. Additionally, the splined engagement of distal clutch 143 with nut 110 and the engagement of teeth 144 on distal clutch 143 with the corresponding teeth in housing 101 prevent independent rotation of nut 110 during this initial mounting of pen body assembly 100 with a new disposable cartridge assembly 300. Thus, axial forces exerted on actuator buttons 407 will cause cartridge housing 304 to threadedly advance along threads 123 of lead screw 120.

After sufficient axial advancement, threads 105 at distal end 103 of pen body housing 101 will engage internal threads 303 at proximal end 301 of cartridge holder assembly 300. As noted above, external threads 105 at distal end 103 of housing 101 have exactly the same pitch and hand as threads 123 on lead screw 120. Hence, further axial forces exerted on actuator button 407 will cause the simultaneous threaded advancement of housing 101 along lead screw 120 and into cavity 305 at proximal end 301 of cartridge holder assembly 300. Thus, because of their identical pitches, lead screw 120 will move proximally relative to pen body housing 101, while pen body housing 101 and cartridge holder assembly 300 are approaching their fully seated and threaded condition.

The assembled pen body assembly 100 and cartridge assembly 300 may be stored until a selected dose of medication is required. Just prior to use, a needle cannula assembly 500 may be threadedly engaged to distal end 302 of cartridge assembly 300. This threaded engagement will cause proximal tip 502 of needle cannula 501 to pierce seal 353 and provide communication with medication 356. Shield 600 may then be removed.

A desired dose of medication 356 is then set by attaching cap 200 to pen body assembly 100 which causes clutch 170 to disengage from anti-rotation ring 160 and permit rotation of dose knob 400 until dosage indicia corresponding to the desired dose appears in window 151 of insert 150. The engagement of button 152 on insert 150 in helical groove 406 in dose knob 400 will cause a threaded retraction of dose knob 400 relative to housing 101 of pen body assembly 100. This threaded retraction of dose knob 400 will cause a simultaneous rotation of driver 450 splined thereto. However, nut 110 will not rotate because saw teeth 144 on distal clutch 143 and the saw teeth on the interior of housing 101 are locked to prevent rotation in that direction. Proximal clutch 141 is splined to nut 110, and hence also will not turn. However, saw teeth 453 at distal end 452 of driver 450 are shaped to allow rotation relative to proximal clutch 141 and provide an audible click for each unit of medication in the selected dose. This is helpful for visually impaired patients who may be required to set doses and administer insulin or other medication to themselves. Annular spring 142 contributes to the engagement that provides these audible clicking sounds.

When the desired dose is set cap 200 is removed from pen body assembly 100, which causes clutch 170 to engage with anti-rotation ring 160 to thereby prevent rotation of end screw 120. Injection is then achieved by merely pushing on actuator button 407. This causes dose knob 400 to turn about helix 406 relative to pen body housing 101, and driver 450 rotates through the same number of degrees. This rotation is opposite to the rotation generated by the dose setting procedure, and the rotational freedom of the clutch assembly 140 is reversed. Thus, as driver 450 turns the previously clicking proximal clutch 141 is locked to and turns with driver 450. This driving movement of proximal clutch 141 causes a corresponding rotational movement of nut 110 because of the splined engagement therebetween. Distal clutch 143 is now free to rotate against the saw teeth on housing 101, and makes an audible clicking indication during injection of medication.

Rotation of lead screw 120 is prevented by tabs 161 on anti-rotation ring 160 mating with grooves 124 in lead screw 120, since anti-rotation ring 160 is prevented from rotating because of its engagement with clutch 170 when cap 200 is removed from pen body assembly 100. Therefore, as nut 110 rotates under the driving action of proximal clutch 141 and driver 450, lead screw 120 will be advanced axially into cartridge holder assembly 300. This axial advancement of lead screw 120 causes distal end 122 thereof to urge plunger 355 distally into cartridge 350, and hence causes medication 356 to be injected through needle cannula 501. Injection will be terminated when proximal end 401 of dose knob 400 engages against proximal end 102 of pen body housing 101.

Upon completion of the injection, needle cannula assembly 500 may be disengaged from cartridge holder assembly 300 and safely discarded. Cap 200 may be mounted over cartridge holder assembly 300, and pen 10 may be stored or carded in a convenient location until the next dose of medication is required. A subsequent dose of medication will be set in exactly the manner as described above. However, for such a subsequent dose, lead screw 120 and plunger 355 will be in a partly advanced position as a starting point. Dose setting and injections can be carried out until all of medication 356 has been used. Cartridge holder assembly 300 may then be threadedly disengaged from pen body assembly 100, and slidably separated from lead screw 120. The separated cartridge holder assembly may then be discarded and replaced as described above.

While the invention has been described with respect to a preferred embodiment, it is apparent that various changes can be made without departing from the scope of the invention as defined by the appended claims. In particular, the pen body assembly may have other driving and/or clutch mechanisms. Additionally, different means for preventing and/or enabling rotation during the dose setting and injection phases may be provided. Similarly, other means for mounting needle cannula to the cartridge assembly may be provided. These various optional constructions will be apparent to those skilled in the art after having read the subject disclosure.

What is claimed is:

1. A medication delivery pen comprising:

a cap;

a medication-containing cartridge assembly having a distal end for receiving said cap of said medication delivery pen and an open proximal end having an array of threads, said medication-containing cartridge assembly further including:

a cartridge having a pierceably sealed distal end, and a plunger in sliding fluid tight engagement within the cartridge at a location distally of said array of threads; and a pen body assembly releasably mountable on said medication-containing cartridge assembly of said medication delivery pen for moving said plunger in said cartridge, said pen body assembly having:

a housing surrounding said pen body assembly and having opposed proximal and distal ends, said distal end having an array of threads dimensioned and having a pitch for threaded engagement with said array of threads at said proximal end of said medication-containing cartridge assembly, a lead screw having a proximal end disposed in said housing, a distal end projecting beyond said distal end of said housing for selective engagement with said plunger, and an array of threads extending between said proximal and distal ends of said lead screw and defining a pitch substantially equal to said pitch of said array of threads at said distal end of said pen body assembly, driver means in said pen body assembly for moving said lead screw distally in said pen body assembly selected amounts, dose setting means for defining specified distances of distal travel for defining specified distances of distal travel for said lead screw corresponding to selected doses of medication to be delivered and causing said driver means to move said lead screw and said plunger in said cartridge distally a defined specified distance corresponding to a selected dose, and clutch means in said pen body assembly for disconnecting said dose setting means from said lead screw when said cap is mounted on said pen body assembly and connecting said dose means to said lead screw means when said cap is not mounted on said pen body assembly.

2. The medication delivery pen of claim 1, wherein said lead screw further comprises at least one anti-rotation groove extending axially therealong for engaging with said clutch means to prevent said lead screw from rotating when said cap is not mounted on said pen body assembly.

3. The medication delivery pen of claim 2, wherein said clutch means comprises:

an anti-rotation ring mounted on said lead screw and having a pair of tabs extending into said anti-rotation groove on said lead screw to prevent said anti-rotation ring from rotating on said lead screw; and a disconnect/connect clutch mounted on said housing between said medication-containing cartridge assembly and said housing to disengage and engage with said anti-rotation ring and thereby disconnect said dose setting means from said lead screw when said cap is mounted on said pen body assembly and connect said dose setting means to said lead screw when said cap is not mounted on said pen body assembly.

4. The medication delivery pen of claim 3, wherein said clutch means further comprises a spring located between said disconnect/connect clutch and said housing to force said disconnect/connect clutch into engagement with said anti-rotation ring when said cap is not mounted on said pen body assembly.

5. The medication delivery pen of claim 2, wherein said clutch means comprises:

an anti-rotation ring mounted on said lead screw having a set of clutch teeth extending in the proximal direction and a pair of tabs extending into said anti-rotation groove on said lead screw to prevent said anti-rotation ring from rotating on said lead screw; and a disconnect/connect clutch mounted on said housing between said medication-containing cartridge assembly and said housing, said disconnect/connect clutch having a set of clutch teeth extending in the distal direction to engage with said set of clutch teeth on said anti-rotation ring, when said cap is not mounted on said pen body assembly.

6. The medication delivery pen of claim 5, wherein said clutch means further comprises a spring located between said disconnect/connect clutch and said housing to force the set of clutch teeth on said disconnect/connect clutch into engagement with the set of clutch teeth on said anti-rotation ring, when said cap is not mounted on said pen body assembly.

7. The medication delivery pen of claim 1, wherein:

said medication-containing cartridge assembly further comprises a pair of slots at a distal end; and said clutch means comprises a pair of protrusions that are received by said slots to prevent said clutch means from rotating with respect to said medication-containing cartridge assembly.

8. The medication delivery pen of claim 7, wherein said lead screw further comprises at least one anti-rotation groove extending axially therealong for engaging with said clutch means to prevent said lead screw from rotating with respect to said medication-containing cartridge assembly, when said cap is not mounted on said pen body assembly.

9. The medication delivery pen of claim 1, wherein said pierceably sealed distal end of said cartridge comprises a pierceable elastomeric seal, and wherein said medication-containing cartridge assembly further comprises needle mounting means at said distal end, said medication delivery pen further comprising a needle cannula assembly having a hub selectively engageable with said needle mounting means and a double-ended needle having opposed proximal and distal points, said proximal point of said needle being dimensioned and disposed to pierce said pierceable elastomeric seal upon engagement with said medication-containing cartridge assembly.

* * * * *